United States Patent [19]

Coltrin et al.

[11] 4,202,992

[45] May 13, 1980

[54] PROCESS FOR PRODUCING HYDROPEROXIDES

[75] Inventors: Michael E. Coltrin, Champaign, Ill.; Yulin Wu, Bartlesville, Okla.

[73] Assignee: Phillips Petroleum Company, Bartlesville, Okla.

[21] Appl. No.: 883,018

[22] Filed: Mar. 3, 1978

[51] Int. Cl.$^2$ .................................................. C07C 179/02
[52] U.S. Cl. ...................................................... 568/575
[58] Field of Search ....................... 260/610 B, 610 A; 568/574, 575

[56] References Cited

U.S. PATENT DOCUMENTS

| | | | |
|---|---|---|---|
| 2,950,237 | 8/1960 | Sharp | 260/610 B |
| 2,966,453 | 12/1960 | Glenn | 260/610 B |
| 3,076,813 | 2/1963 | Sharp | 252/431 |
| 3,484,353 | 12/1969 | Sharp | 260/610 B |
| 4,034,047 | 7/1977 | Angstadt | 260/610 B |

OTHER PUBLICATIONS

Currin, J. Amer. Chem. Soc., vol. 73, #9, p. 4061 (1951).
Dorough, J. Amer. Chem. Soc., vol. 73, #9, pp. 4315–4320.
Maciel et al., J. Amer. Chem. Soc., vol. 92, #14, p. 1451 (1970).
Walker, J. Amer. Chem. Soc., vol. 92, #14, pp. 4235–4245.

*Primary Examiner*—Werren B. Lone

[57] ABSTRACT

Organic hydroperoxides are prepared by reacting an organic compound with oxygen in the absence of light and in the presence of a suitable nickel or copper porphine complex.

22 Claims, No Drawings

PROCESS FOR PRODUCING HYDROPEROXIDES

This invention relates to the production of organic hydroperoxides. It is known that compounds possessing a carbon-hydrogen bond can be oxidized with molecular oxygen to products containing a hydroperoxide group where the original carbon-hydrogen bond was located. Depending upon the particular starting compound, hydroperoxides can be produced with rather high selectivity under suitable oxidation conditions. At the same time, it is recognized that in order to achieve a reasonable degree of selectivity to the desired hydroperoxide, relatively mild conditions need to be utilized because under more severe conditions oxidation of the starting compound can proceed in a nonselective manner and can oxidize the starting compound to such products as carbon dioxide and water under extreme conditions. Under the relatively mild conditions needed for the selective oxidation of the starting compounds to hydroperoxides a penalty is then exacted from the process in terms of the relatively slow reaction rate for the oxidation reaction. Hence, it is desirable to provide a relatively selective oxidation reaction for the production of hydroperoxides while at the same time attaining a faster rate of oxidation under the relatively mild conditions utilized.

Accordingly an object of the present invention is to provide an improved method for producing hydroperoxide compounds.

Another object of the present invention is to provide an oxidative process for producing hydroperoxides without sacrificing selectivity.

Another object of the present invention is to provide a process method for the production of cyclohexylbenzene hydroperoxides by oxidation of cyclohexylbenzene.

Still another object of the instant invention is to provide a novel catalyst composition especially suitable for the oxidative production of hydroperoxides.

Other objects and advantages of the present invention will be apparent from the following disclosure and the appended claims.

In accordance with the present invention hydroperoxides are produced by reacting (1) an organic compound having at least one carbon-hydrogen bond capable of being oxidized to a hydroperoxide-carbon bond and (2) oxygen, in the absence of light and in the presence of a catalytic amount of at least one copper or nickel porphine complex.

In another aspect, in accordance with the present invention there is provided a composition comprising a copper or nickel porphine complex supported upon magnesium oxide or calcium oxide, which composition is particularly useful as a catalyst in the process of the instant invention.

Included among the organic compounds that can be oxidized in accordance with the present invention are polymers having suitable hydrogen-carbon bonds. The preferred polymer starting materials are those consisting essentially of carbon and hydrogen. Especially preferred polymers are polymers of conjugated dienes that have had at least a portion of their unsaturation subjected to hydrogenation. Such hydrogenated polymers of conjugated diolefins and methods for preparing them are known in the art. When polymers are oxidized in accordance with the present invention, the product will be a polymeric hydroperoxide which, of course, may contain more than one hydroperoxide group per polymer molecule. Such polymeric hydroperoxides have utility as polymeric initiator species for free radical type reactions and can serve as the base polymer for graft polymerization reactions utilizing the hydroperoxide group as a reaction site in the polymer chain.

Another class of organic compound which can be used as the starting material in the present invention includes organic compounds having the formula

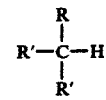

wherein R is hydrogen, an alkyl radical, or an aromatic radical, each R' is individually selected from hydrogen or hydrocarbyl alkyl radical, or the two R' groups are joined to form a saturated hydrocarbyl carbocyclic ring. The preferred compounds have from 3 to 50 carbon atoms. A particularly preferred class of compounds having that formula are the hydrocarbyl compounds having from 3 to 30 carbon atoms. Examples of such hydrocarbyl compounds include propane, 2-methylpropane, 4-methylheptane, 6,8-dipentyleicosane, cyclopentane, cyclohexane, cyclooctane, cyclododecane, methylcyclopentane, 1,4-dimethylcyclohexane, cyclohexylbenzene, and the like.

Another particularly preferred class of organic compounds of the formula

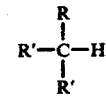

as above defined, are those aromatic compounds having 8 to 50 carbon atoms per molecule where R is an aromatic radical. The aromatic radical can include any sort of substitution that does not prevent the oxidation of the present invention. Examples of suitable substitutes include halogen, nitro, alkyl, carboxyalkyl and the like. Examples of such compounds include toluene, p-xylene, m-xylene, ethylbenzene, p-chlorotoluene, p-nitrotoluene, 3-(4-methylphenyl) propanoic acid, isopropylbenzene, cyclopentylbenzene, cyclohexylbenzene, and the like. The most preferred of these aromatic compounds are the hydrocarbyl aromatic, i.e., those containing only carbon and hydrogen.

The molecular hydroperoxides like the polymeric hydroperoxides generally have utility as initiators in free radical polymerization systems. Furthermore, generally such hydroperoxides can be treated further under acidic hydrolysis conditions to provide cleavage products such as hydroxy compounds or carbonyl compounds. In addition such hydroperoxides generally can also be utilized as catalyst components for the epoxidation of olefinic compounds in the presence of tungsten or molybdenum or their compounds.

The catalyst which is utilized according to the instant invention to provide an increase in the rate of oxidation in the production of hydroperoxide compounds is a nickel or copper porphine complex of the following general formula:

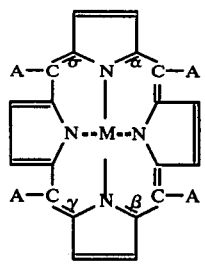

wherein M is Ni (II) or Cu (II) and each A is individually selected from the group consisting of hydrogen, alkyl radicals, and aryl radicals; and at least one A is an aryl radical. The aryl radical can be a polycyclic aryl radical, for example, 1-naphthyl, 2-naphthyl, anthracyl, phenanthryl, and the like or a monocyclic aryl radical, for example, phenyl, chlorophenyl, dichlorophenyl, tolyl, N-N-dimethylaminophenyl, hydroxyphenyl, carboxyphenyl, and the like. The alpha, beta, gamma and delta positions in the above formula are often designated in the art as meso positions. Methods of making the nickel or copper complexes of the porphines are well known in the art and many of the complexes are commercially available. Examples of suitable nickel or copper porphine complexes which can be utilized as oxidation catalysts in the instant invention include α,β,γ,δ,-tetraphenylporphineatonickel (II),
α,β,γ,δ,-tetra(4-carboxyphenyl)porphinatonickel (II),
α,β,γ,δ,-tetra(4-methoxyphenyl)porphinatonickel (II),
α,β,γ,δ,-tetra(4-chlorophenyl)porphinatonickel (II),
α,β,γ,δ,-tetra(4-hydroxyphenyl)porphinatonickel (II),
α,β,γ,δ,-tetra(2,4-dichlorophenyl)porphinatonickel (II),
α,β,γ,δ,-tetra(3,4-dichlorophenyl)porphinatonickel (II),
α,β,γ,δ,-tetra(4-methylphenyl)porphinatonickel (II),
α,β,γ,δ,-tetraanthracylporphinatonickel (II),
α,β,γ,δ,-tetra(1-naphthyl)porphinatonickel (II) and the corresponding copper (II) complexes.

The oxidation reaction of the present invention is carried out in the absence of light. While it is expected that if light were present many organic compounds could be converted to hydroperoxide, it is unknown whether such a reaction would exhibit the advantages in regard to selectivity and rate that are produced by the present invention.

The amount of porphine complex catalyst employed in the instant invention can vary widely. Any catalytic amount can be employed. Generally the amount of catalyst utilized is in the range of about 0.001 to about 5 weight percent, and preferably in the range of about 0.05 to about 1 weight percent, based upon the weight of the organic compound to be oxidized.

Any suitable amount of oxygen can be employed. Preferably, enough oxygen is employed to obtain maximum conversion of the organic reactant or reactants. The amount of oxygen employed can be expressed in terms of the mole ratio of oxygen to that of organic compound that is to be oxidized. Generally, this ratio is in the range of from about 0.0005/1 to about 20/1 or higher, and preferably in the range of about 0.001/1 to about 2/1. The oxygen may be introduced into the reaction zone in any manner that will result in oxygen contacting the material to be oxidized. For example, the reaction mixture can be merely stirred under an oxygen atmosphere or oxygen can be bubbled through the reaction mixture. Air as well as other mixtures of gases with oxygen may be utilized as the source of oxygen.

The temperature utilized in the instant invention can vary widely. Of course as mentioned earlier, lower temperatures tend to result in better selectivity to hydroperoxides. Generally, the temperature should be in the range of about 25° C. to about 200° C., preferably about 90° C. to about 160° C. The time employed depends only upon the temperature employed and the degree of conversion that one desires. At prolonged times, the yields of hydroperoxides increases reaching a maximum and then declines because of decomposition of the hydroperoxides. Generally, the heating is conducted for a time in the range of about 5 minutes to about 2 days.

If desired, a suitable reaction diluent may be employed in carrying out the instant invention. Examples of suitable diluents include monohydric alcohols having from 1 to 8 carbon atoms, linear alkane hydrocarbons having from 4 to 12 carbon atoms, and sulfolane. Of course preferably the diluents will be selected that don't adversely affect the oxidation rate or the selectivity of the reaction stream.

The presence of a small amount of certain hydroperoxides in the initial reaction mixture has been found to reduce the induction period, i.e., the period of heating required before any significant oxidation begins. Hydroperoxides that are suitable initiators are those which decompose under the reaction conditions quickly enough to reduce the induction periods. Examples of suitable initiators include cumene hydroperoxide and cyclohexylbenzene hydroperoxide. Generally, hydroperoxide initiators are effective in amounts in the range of about 0.5 to about 1.5 weight percent of the weight of the material to be oxidized.

With most of the porphine complex catalysts which can be employed in this invention, the addition of small amounts of the hydroxides, oxides, or carbonates of alkali or alkaline earth metals to the reaction mixture has a beneficial effect upon both the rate of oxidation and the selectivity to hydroperoxides. Generally the amount of such alkali or alkaline earth metal compound employed is in the range of about 0.05 to about 0.25 weight percent based upon the weight of the material to be oxidized.

While water can be present in the initial reaction mixture of the instant invention, preferably the amount of water is not greater than about 0.5 weight percent based upon the weight of the material to be oxidized. Larger amounts of water tend to have an adverse effect upon the selectivity of the oxidation.

The present invention can be carried out by either a batch or a continuous process. In using a batch process, it is advantageous to recycle small portions of previous reaction product as the hydroperoxide therein tends to reduce the induction period that would otherwise result.

The present invention can be carried out in a continuous fashion by passing the reactants through a reaction zone containing the porphine complex catalyst supported on a suitable inert support. Alkaline earth metal oxides such as magnesium or calcium oxide are examples of suitable supports. Generally, the amount of porphine complex deposited in the suitable support is in the range of about 0.01 to about 10 weight percent based upon the weight of the support.

The reaction product mixture obtained in accordance with the instant invention will contain hydroperoxide, unreacted starting material, and small amounts of other reaction by-products along with the reaction diluent, if a diluent was employed. When using a batch process for the oxidation reaction, it is often possible to recover the catalyst by filtration from the reaction product mixture. The hydroperoxide can be recovered using any suitable recovery technique conventionally used for recovering such hydroperoxide compounds from such mixtures, for example, extraction, absorption, or distillation.

The present invention is particularly suitable for the production of cyclohexylbenzene hydroperoxides from cyclohexylbenzene. The components of reaction product mixture resulting from the oxidation of cyclohexylbenzene in accordance with this invention have been found to include 1-, 2-, 3-, and 4-phenylcyclohexyl hydroperoxide, methylcyclopentylbenzene hydroperoxide, phenylcyclohexanols, phenylcyclohexanone, hexanophenone, phenylcyclohexene, heavies, unreacted cyclohexylbenzene, and diluent, when diluent is employed. The major cyclohexylbenzene hydroperoxide produced is 1-phenylcyclohexyl hydroperoxide.

It is particularly desirable to separate the major portion of the cyclohexylbenzene hydroperoxides produced in accordance with this invention from the other components of the reaction product mixture and then subject cyclohexylbenzene remaining in the reaction product mixture to additional oxidation in accordance with the instant invention.

One effective method for separating the cyclohexylbenzene hydroperoxide produced in accordance with this invention from the other components of the reaction product mixture involves extraction with a mixture of methanol and water. Generally, the methanol-water mixture having higher methanol to water weight ratios resulted in the extraction of greater amounts of the hydroperoxide. After the extraction the aqueous methanol extract can be evaporated to provide the hydroperoxide products.

The present invention and its advantages will be further understood by reference to the following examples which follow. In these examples, unless it is noted otherwise, weight percent values are based upon the weight of the cyclohexylbenzene reactant.

EXAMPLE I

Two control runs were carried out in which cyclohexylbenzene (CHB) was oxidized at 120° C. in a 300 ml stainless steel autoclave under an initial oxygen pressure of 200–250 psig. In one run (run no. 1) the oxidation was carried out in the absence of any oxidation catalysts or initiator or aqueous base. In run no. 2, the oxidation reaction was carried out in the presence of 0.89 weight percent initiator, cyclohexylbenzene hydroperoxide ($CHBO_2H$), and 0.29 weight percent of a 50% by weight aqueous sodium hydroxide solution. Both runs were carried out for a period of about six hours. The results obtained in control runs 1 and 2 are presented below in Table I.

Table I

| Run No. | CHB, g. | Ave. Rate wt. %/hr[a] | Conv., mol % | Sel., mol % |
|---|---|---|---|---|
| 1 | 100 | 1.64 | 10.3 | 94.5 |

Table I-continued

| Run No. | CHB, g. | Ave. Rate wt. %/hr[a] | Conv., mol % | Sel., mol % |
|---|---|---|---|---|
| 2 | 104 | 1.87 | 10.4 | 95.5 |

[a]Average rate of cyclohexylbenzene hydroperoxide production in wt. %/hr. based on total reaction mixture. The value is based on an iodometric titration of weighed samples of the reaction mixture.

The results for run no. 1 show a relatively low rate of oxidation and a 45 minute induction period at the beginning of the run was also observed. This result typifies oxidation results obtained in the absence of an initiator and catalyst. In run no. 2, the presence of the initiator and aqueous base essentially eliminated the induction period but increased the rate of oxidation only slightly.

EXAMPLE II

Additional runs were carried out utilizing the 300 ml stainless steel autoclave at a temperature of 120° C. under an initial oxygen pressure of 200–225 psig. The runs of this example utilized metal complexes of meso-tetraphenylporphine or the meso-tetraphenylporphine itself as the oxidation catalyst. Each of the runs utilized 60 grams of cyclohexylbenzene as the starting material, 0.42 weight percent of a 50% aqueous sodium hydroxide solution and 1.0 weight percent of the oxidation initiator ($CHBO_2H$). The results obtained in the oxidation runs of this example are presented below in Table II.

Table II

| Run No. | Catalyst Type | wt. % | Ave. Rate wt. %/hr. | Reaction Time, hr. | Conv., mol % | Sel., mol % |
|---|---|---|---|---|---|---|
| 3 | TPP[a] | 0.20 | 2.65 | 4.33 | 7.8 | 100 |
| 4 | CoTPP[b] | 0.22 | 4.55 | 0.35 | 26.7 | 4.9 |
| 5 | CuTPP[c] | 0.22 | 8.78 | 0.5 | 7.3 | 51.8 |
| 6 | FeTPPBr[d] | 0.24 | 6.21 | 1.27 | 11.1 | 71.3 |
| 7 | NiTPP[e] | 0.22 | 8.43 | 1.5 | 13.6 | 80.7 |

[a]TPP = meso-tetraphenylporphine
[b]CoTPP = $\alpha, \beta, \gamma, \delta$-tetraphenylporphinatocobalt (II).
[c]CuTPP = $\alpha, \beta, \gamma, \delta$-tetraphenylporphinatocopper (II).
[d]FeTPPBr = $\alpha, \beta, \gamma, \delta$-tetraphenylporphinatoiron (III) bromide.
[e]NiTpp = $\alpha, \beta, \gamma, \delta$-tetraphenylporphinatonickel (II).

The results shown in Table II demonstrate that although meso-teraphenylporphine gives very high selectivity in the oxidation reaction, the rate of oxidation is only slightly greater than the control run of Example I utilizing no catalyst. It is also observed (run 4) that $\alpha,\beta,\gamma,\delta$,-tetraphenylporphinatocobalt (II) gave high conversion of the starting material but very low selectivity and only a moderate increase in the rate of oxidation compared to run 3. The corresponding iron complex of run no. 6 gave an improvement in the rate of oxidation which also was moderate. It is observed that the nickel complex gave the best overall results while the copper complex with meso-tetraphenylporphine gave slightly poorer results than the nickel complex under these conditions. Thus, the nickel and copper tetraphenylporphine complexes have been shown to significantly improve the rate of oxidation compared to the control runs while still giving a reasonable degree of selectivity in the oxidation reaction to hydroperoxide.

The meso-tetraphenylporphine complexes utilized in the instant example were prepared by reacting suitable metal salts with meso-tetraphenylporphine in propionic acid media. The cobalt, copper and nickel complexes are also available commercially.

EXAMPLE III

Additional runs were carried out according to the instant invention utilizing copper and nickel tetraanthracylporphine complexes. In the runs of this example, the oxidation reactions were carried out utilizing the 300 ml stainless steel autoclave reactor at 120° C. (except where noted) under an initial oxygen pressure of 200 psig. Again, the oxidation reactant was cyclohexylbenzene (60 grams) in each of the oxidation runs. Each run was also carried out in the presence of 1.1 weight percent initiator ($CHBO_2H$). The results obtained in these runs are shown below in Table III.

Table III

| Run No. | Catalyst Type | wt. % | Ave. Rate wt. %/hr. | Reaction Time, hr. | Conv. mol % | Sel., mol % |
|---|---|---|---|---|---|---|
| 8 | None | 0 | 2.80 | 4.25 | 11.4 | 90.4 |
| 9 | TAP[b] | 0.20 | 1.83 | 3.67 | 4.9 | ~100 |
| 10 | CuTAP[c] | 0.20 | 4.30 | 3.67 | 15 | 92 |
| 11 | NiTAP[d] | 0.20 | 2.99 | 5.62 | 15.3 | 94 |
| 12[a] | CuTAP | 0.20 | 3.80 | 4.5 | 17.1 | 88 |
| 13 | CuTAP | 0.20 | 4.35 | 4.0 | 17.5 | 89 |
| 14 | CuTAP | 1.0 | 4.09 | 3.23 | 14 | 85 |
| 15 | CuTAP | 2.0 | 4.95 | 1.77 | 10 | 75 |
| 16 | CuTAP/MgO[e] | 2.5 | 4.32 | 3.27 | 14.2 | 90 |

[a]Employed 0.13 wt. %, of aq. NaOH (50% by wt.).
[b]TAP = meso-tetraanthracylporphine.
[c]CuTAP = α, β, γ, δ-tetraanthracylporphinatocopper (II).
[d]NiTAP = α, β, γ, δ-tetraanthracylporphinatonickel (II).
[e]5 wt. % of CuTAP deposited on MgO.

Again, the copper and nickel complexes gave better rates of oxidation than the control runs of Example I. In addition, it can be noted that the copper (II) tetraanthracylporphine complex gave a higher selectivity to hydroperoxide than the corresponding meso-tetraphenylporphine complex of copper (II) although at a slower rate of oxidation. It is also seen that CuTAP supported on the magnesium oxide can give good results in catalyzing the oxidation reaction according to the instant invention. However, it was found that the use of alumina for catalyst support was much less effective than the use of magnesium oxide. When alumina was utilized as the support material, only a trace of hydroperoxide was formed. Furthermore, it can also be seen the presence of sodium hydroxide had a moderately detrimental effect on the oxidation of cyclohexylbenzene when the reaction was catalyzed by copper (II) tetraanthracylprophine (run no. 12). Both the rate of oxidation and selectivity to hydroperoxide were lower when sodium hydroxide was present in the oxidation run.

EXAMPLE IV

Three runs were conducted utilizing the copper (II) tetraanthracylporphine complex to demonstrate the feasibility of recovery and recycle of the complex to additional oxidation runs. In each oxidation run, the starting material to be oxidized was cyclohexylbenzene (60 grams). The oxidation reaction was conducted at 115° C. under pure oxygen at an initial pressure of 200 psig in the presence of 1.2 wt. % $CHBO_2H$ initiator. The results of the runs demonstrating recycle of the catalyst are presented below in Table IV.

Table IV

| Run No. | Recycle No. | Catalyst, g. charge | Catalyst, g. recover | Catalyst, g. make-up | Ave. Rate wt. %/ hr. | Reaction Time, hr. | Conv. mol % | Sel. mol % |
|---|---|---|---|---|---|---|---|---|
| 17 | 0 | 0.12 | 0.078 | 0.042 | 3.26 | 4.87 | 14 | 99 |
| 18 | 1 | 0.12 | 0.093 | 0.027 | 2.70 | 4.87 | 12 | 98 |
| 19 | 2 | 0.12 | 0.098 | — | 2.82 | 5.83 | 16 | 91 |

The results shown in Table IV indicate that catalytic activity for the copper (II) tetraanthracylporphine complex was fairly constant for the first and second cycles. The color of the complex was observed to change from black to a dark brown upon being recycled.

EXAMPLE V

Other runs were conducted according to the instant invention utilizing as the oxidation catalyst 5 weight percent of the complex copper (II) mesotetrakis(4-carboxyphenyl)porphine on magnesium oxide. In each of the oxidation runs, cyclohexylbenzene (60 grams) was the hydrocarbon undergoing oxidation and each run utilized 1.10 weight percent of initiator ($CHBO_2H$) for the oxidation. The oxidations were conducted at 120° C. under an initial oxygen pressure of 200 psig. The results obtained in the runs of the instant example are presented below in Table V.

Table V

| Run No. | Catalyst,[a] g. | Ave. Rate wt. %/hr. | Reaction Time, hr. | Conv., mol % | Sel., mol % |
|---|---|---|---|---|---|
| 20 | 0.078 | 3.25 | 4.88 | 14 | 100 |
| 21 | 0.102 | 3.47 | 6.5 | 22 | 93 |
| 22 | 0.246 | 3.19 | 6.38 | 24 | 77 |

[a]5 wt. % of α, β, γ, δ-tetra(4-carboxyphenyl)porphinatocopper (II) on magnesium oxide.

The results shown in Table V indicate that the copper (II) mesotetrakis-(4-carboxyphenyl)porphine complex deposited on magnesium oxide was not as active as the previously examined complexes of the instant invention in increasing the rate of oxidation but still gave good conversion and high selectivity to the desired hydroperoxide product. The catalyst utilized in the runs of this example was observed to be soluble in water and insoluble in organic solvents. These solubility characteristics are helpful in recycling the catalysts and in purifying the product from catalyst residues by water washing procedures and the like.

What is claimed is:

1. A process for producing cyclohexylbenzene hydroperoxide comprising reacting cyclohexylbenzene and oxygen in the absence of light and in the presence of at least one copper or nickel porphine complex under conditions suitable for producing said hydroperoxide, said conditions including a temperature in the range of about 25° C. to about 200° C. and a pressure in the range of about 0 psig to about 1000 psig wherein said porphine complex has the formula:

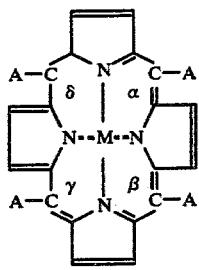

where M is Ni (II) or Cu (II), each A is individually selected from the group consisting of hydrogen, alkyl, or aryl radicals, and at least one A is an aryl radical.

2. A process according to claim 1 wherein said porphine complex is selected from the group consisting of
α,β,γ,δ-tetraphenylporphinatonickel (II),
α,β,γ,δ-tetra(4-carboxyphenyl)porphinatonickel (II),
α,β,γ,δ-tetra(4-methoxyphenyl)porphinatonickel (II),
α,β,γ,δ-tetra(4-chlorophenyl)porphinatonickel (II),
α,β,γ,δ-tetra(4-hydroxyphenyl)porphinatonickel (II),
α,β,γ,δ-tetra(2,4-dichlorophenyl)porphinatonickel (II),
α,β,γ,δ-tetra(3,4-dichlorophenyl)porphinatonickel (II),
α,β,γ,δ-tetra(4-methylphenyl)porphinatonickel (II),
α,β,γ,δ-tetraanthracylporphinatonickel (II),
α,β,γ,δ-tetra(1-naphthyl)porphinatonickel (II),
α,β,γ,δ-tetraphenylporphinatocopper (II),
α,β,γ,δ-tetra(4-carboxyphenyl)porphinatocopper (II),
α,β,γ,δ-tetra(4-methoxyphenyl)porphinatocopper (II),
α,β,γ,δ-tetra(4-chlorophenyl)porphinatocopper (II),
α,β,γ,δ-tetra(4-hydroxyphenyl)porphinatocopper (II),
α,β,γ,δ-tetra(2,4-dichlorophenyl)porphinatocopper (II),
α,β,γ,δ-tetra(3,4-dichlorophenyl)porphinatocopper (II),
α,β,γ,δ-tetra(4-methylphenyl)porphinatocopper (II),
α,β,γ,δ-tetraanthracylporphinatocopper (II),
α,β,γ,δ-tetra(1-naphthyl)porphinatocopper (II).

3. A process according to claim 2 wherein said reaction is conducted at a temperature in the range of about 90° to about 160° C.

4. A process according to claim 3 wherein said porphine complex is selected from the group consisting of
α,β,γ,δ-tetraphenylporphinatocopper (II)
α,β,γ,δ-tetraphenylporphinatonickel (II)
α,β,γ,δ-tetraanthracylporphinatocopper (II)
α,β,γ,δ-tetraanthracylporphinatonickel (II)
α,β,γ,δ-tetra(4-carboxyphenyl)porphinatocopper (II).

5. A process according to claim 4 wherein the amount of said porphine complex is in the range of about 0.001 to about 5 weight percent of the weight of the cyclohexylbenzene, the molar ratio of oxygen to cyclohexylbenzene before the reaction is begun is in the range of about 0.005/1 to about 20/1, and the reaction is carried out in a suitable diluent.

6. A process according to claim 5 wherein said initial reaction mixture contains an aqueous sodium hydroxide solution containing approximately equal weight of water and sodium hydroxide in an amount less than about 0.5 weight percent of said cyclohexylbenzene.

7. A process according to claim 6 wherein said porphine complex is selected from the group consisting of α,β,γ,δ-tetraphenylporphinatocopper (II); α,β,γ,δ-tetraphenylporphinatonickel (II); and α,β,γ,δ-tetraanthracylporphinatocopper (II).

8. A process according to claim 7 wherein the initial reaction mixture contains about 0.5 to about 1.5 weight percent of a hydroperoxide initiator based upon the weight of the cyclohexylbenzene.

9. A process according to claim 8 wherein said hydroperoxide initiator is a cyclohexylbenzene hydroperoxide.

10. A process according to claim 8 wherein said hydroperoxide initiator is cumene hydroperoxide.

11. A process according to claim 6 wherein the initial reaction mixture contains about 0.5 to about 1.5 weight percent of a hydroperoxide initiator based upon the weight of the cyclohexylbenzene.

12. A process according to claim 11 wherein said hydroperoxide initiator is a cyclohexylbenzene hydroperoxide.

13. A process according to claim 11 wherein said hydroperoxide initiator is cumene hydroperoxide.

14. A process according to claim 5 wherein said porphine complex is supported on magnesium oxide.

15. A process according to claim 14 wherein said porphine complex is α,β,γ,δ-tetraanthracylporphinatocopper (II) or α,β,γ,δ-tetra(4-carboxyphenyl)porphinatocopper (II).

16. A process according to claim 1 wherein said porphine complex is supported on magnesium oxide.

17. A process according to claim 16 wherein said porphine complex is α,β,γ,δ-tetraanthracylporphinatocopper (II) or α,β,γ,δ-tetra(4-carboxyphenyl)porphinatocopper (II).

18. A process according to claim 3 wherein said porphine complex is α,β,γ,δ-tetraphenylporphinatocopper (II).

19. A process according to claim 3 wherein said porphine complex is α,β,γ,δ-tetraphenylporphinatonickel (II).

20. A process according to claim 3 wherein said porphine complex is α,β,γ,δ-tetraanthracylporphinatonickel (II).

21. A process according to claim 3 wherein said porphine complex is α,β,γ,δ-tetraanthracylporphinatocopper (II).

22. A process according to claim 3 wherein said porphine complex is α,β,γ,δ-tetra(4-carboxylphenyl)porphinatocopper (II).

* * * * *